(12) United States Patent
Sanchez del Rio Saez et al.

(10) Patent No.: US 8,766,189 B2
(45) Date of Patent: Jul. 1, 2014

(54) OPTICAL SYSTEM, METHOD AND COMPUTER PROGRAM FOR DETECTING THE PRESENCE OF A LIVING BIOLOGICAL ORGANISM

(75) Inventors: José Sanchez del Rio Saez, Madrid (ES); Raúl Veleiro Aradas, Madrid (ES); Nicolás Antequera Rodriguez, Madrid (ES)

(73) Assignee: Hanscan IP B.V., Amsterdam (NL)

( * ) Notice: Subject to any disclaimer, the term of this patent is extended or adjusted under 35 U.S.C. 154(b) by 399 days.

(21) Appl. No.: 13/121,183

(22) PCT Filed: Oct. 29, 2008

(86) PCT No.: PCT/ES2008/000669
§ 371 (c)(1),
(2), (4) Date: Apr. 28, 2011

(87) PCT Pub. No.: WO2010/034848
PCT Pub. Date: Apr. 1, 2010

(65) Prior Publication Data
US 2012/0119089 A1 May 17, 2012

(30) Foreign Application Priority Data

Sep. 26, 2008 (ES) .................... 200802739

(51) Int. Cl.
*G01J 5/20* (2006.01)
(52) U.S. Cl.
USPC ....................................... 250/338.4
(58) Field of Classification Search
USPC ................ 250/338.4, 372; 382/115
See application file for complete search history.

(56) References Cited

U.S. PATENT DOCUMENTS 6,560,352 B2 * 5/2003 Rowe et al. ............. 382/115
6,813,010 B2 11/2004 Kono et al.
(Continued)

FOREIGN PATENT DOCUMENTS

| EP | 0150330 A2 | 8/1985 |
| EP | 1654984 A2 | 5/2006 |

(Continued)

OTHER PUBLICATIONS

International Search Report, mailing date Jun. 5, 2009, for corresponding International Application No. PCT/ES2008/000669.

*Primary Examiner* — Christine Sung
(74) *Attorney, Agent, or Firm* — Intellectual Property Law Group LLP (57) ABSTRACT

The system is comprised of at least one pair of light sources (1;2;3) that emit pulsed electromagnetic radiation in the near-infrared zone; at least one pair of light sources (1;2;3) that emit radiation in the near-ultraviolet zone; at least one photodetector (4) with the absorption band located in the near-infrared zone, for detecting the pulsed radiation transmitted and reflected on the biological element, on the basis of the pulsed radiation emitted by the pair of light sources that emit the radiation in the near-infrared; at least one photodetector (5) with the absorption band located in the near-ultraviolet zone, for detecting the pulsed radiation transmitted and reflected on the biological element, on the basis of the pulsed radiation emitted by the pair of light sources (1;2;3) that emit the radiation in the near-ultraviolet zone; a control unit (8(*c*)) that interprets the pulsed radiation transmitted and reflected on the biological element; and a processing unit (8(*d*)) that determines if it is a living biological element, on the basis of the radiation interpreted by the control unit.

21 Claims, 9 Drawing Sheets

(56) References Cited

U.S. PATENT DOCUMENTS

| | | | |
|---|---|---|---|
| 6,816,605 B2 * | 11/2004 | Rowe et al. | 382/115 |
| 2003/0078504 A1 * | 4/2003 | Rowe | 600/476 |
| 2004/0184641 A1 | 9/2004 | Nagasaka et al. | |
| 2005/0265586 A1 | 12/2005 | Rowe et al. | |
| 2006/0210120 A1 * | 9/2006 | Rowe et al. | 382/115 |
| 2007/0253607 A1 | 11/2007 | Higuchi | |
| 2008/0037001 A1 * | 2/2008 | Yokoyama et al. | 356/51 |
| 2009/0060296 A1 * | 3/2009 | Mainguet | 382/124 |
| 2011/0298911 A1 * | 12/2011 | Maro et al. | 348/77 |
| 2013/0021596 A1 * | 1/2013 | Rowe et al. | 356/51 |

FOREIGN PATENT DOCUMENTS

| | | |
|---|---|---|
| EP | 1834581 A1 | 9/2007 |
| EP | 1898338 A2 | 3/2008 |
| ES | 2110841 T3 | 2/1998 |
| WO | WO 8901758 A1 | 3/1989 |
| WO | WO 9637259 A1 | 11/1996 |
| WO | WO 0116577 A1 | 3/2001 |
| WO | WO 02084605 A2 | 10/2002 |
| WO | WO 2005059805 A2 | 6/2005 |
| WO | WO 2006067006 A1 | 6/2006 |
| WO | WO 2007027579 A2 | 3/2007 |

* cited by examiner

OPTICAL SYSTEM, METHOD AND COMPUTER PROGRAM FOR DETECTING THE PRESENCE OF A LIVING BIOLOGICAL ORGANISM

CROSS-REFERENCE TO RELATED APPLICATIONS

This application is a U.S. National Phase application, under 35 U.S.C. §371, of International Application no. PCT/ES2008/000669, with an international filing date of Oct. 29, 2008 and claims benefit of Spain Application no. P200802739 filed on Sep. 26, 2008, and which are hereby incorporated by reference for all purposes.

This invention relates to a procedure for detecting the presence of a living biological element. The invention also relates to an optic system and a computer programme that are suitable for carrying out the procedure described herein.

To be more specific, the system uses a pulsed electromagnetic radiation emitter—receiver system with the emission-reception band located in the near-infrared zone and the ultraviolet zone close to the electromagnetic spectrum, to be used as a means for detecting life and personal identification. This system is purely optical in nature and may be integrated in a biometric sensor, such as in a fingerprint sensor that may function by radio frequency or by electrical capacity, or in the optical for detecting blood capillaries. It may also be used on an independent basis as a biometric system for autonomous personal identification.

This invention is used as means of detecting that the user that is to be identified with a biometric system is the user in question and considerably eliminates impersonation attempts. It therefore falls within the scope of biometrics and as it makes use of the transmission and reflection of near infra-red radiation and the reflection of UV-A radiation with different wavelengths in human tissue, it also falls within the scope of optical life detection transmittance and reflection sensors, which are characteristic of Photonic Biometric Spectroscopy.

BACKGROUND OF THE INVENTION

Nowadays, there are many fraud attempts that involve the impersonation of a person's identity. Biometrics uses the unique biological characteristics of the individual in identifying same (they are unique and non-repeatable), such as the fingerprint, the vein pattern on the palm of the hand or the rhythm of the heartbeat. Fields like Microelectronics, Photonics or Information Technology produce numerous biometric systems each year, with the intention of supplanting them as access systems.

The more biometric systems that arise, the more attempts there are at forging the biometric characteristics in question in order to "trick" the biometric sensor. Therefore, by means of artificial, lifeless materials, the hacker attempts to supplant the identity of the user that in theory will be identified as a user already registered in the access system. These attempts at fooling the biometric system are the reason behind the fear and mistrust displayed by institutions that need top security, such as banks, restricted access platforms or biometric payment gateways, as well as all electronic or information technology systems that require a biometric code to function, etc. Therefore, there are also many attempts at creating life detection systems that distinguish between the living person with their unique biometric characteristics and any replacement artificial material.

U.S. Pat. No. 6,813,010 B2 describes a biometric vein sensor known as PALM VEIN SECURE, by Fujitsu, which is used as a personal identification system. This system uses the blood capillary pattern on the palm of the hand as the unique biometric receiver element. A set of LEDs with an emission spectrum in the near-IR illuminates the palm of the hand and a CCD camera captures the image that corresponds to the radiation reflected on it. This image presents dark straight and curved sections that represent the map of blood capillaries in the hand and are due to the areas that absorb the near-IR radiation emitted by the LEDs that has not been reflected on the palm of the user's hand. The absorption of the near-IR radiation by the veins in the hand is due to the deoxidised blood haemoglobin in the blood, which presents an absorption peak of 760 nm on the electromagnetic spectrum.

As we have said before, the biometric element in Fujitsu's vein sensor, PALM VEIN SECURE, is the map of blood capillaries on the palm of the hand. At first sight, it is a biometric element that is very hard to copy because it is hidden within the tissues of the hand, but that is only at first sight, because it has already been "fooled".

U.S. Pat. No. 6,813,010 describes a biometric sensor manufactured by HITACHI. This sensor captures as the unique biometric element the veins on a single finger of the hand of the user in question. Thus, the sensor detects the near-infrared radiation that is transmitted through the finger and emitted by LEDs whose emission band is in the near-IR and optimises the intensity of the light that arrives at the finger, so that a sharper vein pattern is obtained, making subsequent recognition easier. However, this characteristic vein pattern is simpler than the one that is gathered by FUJITSU's vein sensor for the palm of the hand, because the capture area is smaller and the mesh of capillaries is less ramified. Therefore, it is easier to copy, using the same forging procedure as is used with the FUJITSU sensor.

We have provided a brief description of two of the biometric sensors on the market that present the unique biometric element that is most difficult to forge (vein pattern). There are many others that appear in the literature and allow to identify people, such as the fingerprint sensors and those that operate according to facial recognition or hand geometry recognition, etc. Their biometric elements are unique (or almost unique), but they have the disadvantage that they are easy to replicate (using photographs, silicon fingerprints, silicon hands, etc.).

To date, only a few life detection systems for biometric sensors have been described in the literature. The majority are low-cost and are not implemented in biometric sensors because they can be easily "fooled" using simple substitution techniques. Hence, for example, when the human pulse is detected optically, it may be easily achieved by using a sheet of paper in a characteristic colour that absorbs part of the light beam that reaches the detector. Another example is the measurement of the bioimpedance of human tissue with an impedance measuring device. This measurement may be obtained using a material with an impedance that is characteristic of the characteristic biological element in question.

On the other hand, other much more advanced life detection systems that measure skin roughness, the electrical and optical characteristics of its internal layers, etc. are very expensive (they use spectrophotometers, mobile optical systems, optic fibres and waveguides, magnifying macro-lenses, CCD linear matrixes, etc.) and therefore they are not used in the biometric sensors that are available on the market.

The highlights among these developments are the following patent documents: WO 2007/027579, WO 2005/059805 and US 2005/0265586 (by the company LUMIDGIN) which employ various light sources (polarized or otherwise) in the infrared and near-ultraviolet spectrum (between 300 and 1100 nm) to observe light reflectance through skin and underlying tissue and identify certain physiological parameters that are characteristic of the individual.

European Patent EP 150330 is based on the roughness model of the tissue in the internal layer of the skin covered by the epidermal tissue, using near-infrared radiation and the analysis of different optical properties.

International patent no. WO 02/084605 also presents a device that employs light sources in the near infrared and near-ultraviolet zones of the electromagnetic spectrum to measure the absorption and reflection of light energy under the epidermis. Other related documents are as follows: WO 89/01758, EP 1834581 and US 2007/0253607. As mentioned before, these are systems that use optical elements of medium or high cost.

DESCRIPTION OF THE INVENTION

On the basis of the above, the objective of this invention is to provide an optical system for detecting the presence of a living biological element that is low-cost and more reliable.

This objective is achieved in accordance with claim 1, providing an optical system for detecting the presence of a living biological element, composed of at least a pair of light sources that emit pulsed electromagnetic radiation with the emission band located in the near-infrared zone of the electromagnetic spectrum; at least a pair of light sources that emit pulsed electromagnetic radiation with the emission band located in the near-ultraviolet zone of the electromagnetic spectrum; at least one photodetector with the absorption band located in the near-infrared zone of the electromagnetic spectrum, to detect the pulsed radiation transmitted and reflected in the biological element, on the basis of the pulsed radiation emitted by the pair of light sources that emit the radiation with the emission band located in the near-infrared zone; at least one photodetector with the absorption band located in the near-ultraviolet zone of the electromagnetic spectrum, to detect the pulsed radiation transmitted and reflected in the biological element, on the basis of the pulsed radiation emitted by the pair of light sources that emit the radiation with the emission band located in the near-ultraviolet zone; a control unit, connected to the pairs of light sources and to the photodetectors, which interprets the pulsed radiation that is transmitted and reflected in the biological element and detected by the photodetectors; and a processing unit, connected to the control unit, which determines if the biological element is a living biological unit on the basis of the radiation that is interpreted by the control unit.

This provides a system that allows to detect the presence of a living biological element and distinguish it from one that is not living, using the properties of transmission and reflection of the pulsed electromagnetic and quasi-coherent radiation on human epithelial tissue (skin and veins), whereas this system is low-cost and highly reliable.

More specifically, in order to solve the problems of cost and security described above, a biometric optical sensor for detecting life has been designed on the basis of the transmission and reflection of pulsed near-infrared radiation and the reflection, also pulsed, of the UV-A radiation with the epithelial tissue of the biometric recognition element (in other words, the finger of the user in question). This optical sensor may be integrated in a radiofrequency fingerprint sensor, but it may also be integrated into any other biometric sensor for personal identification, such as the one that detects the blood capillaries on the palm of the user's hand, and it measures the optical parameters mentioned above using the pulsed nature of the near-infrared and near-ultraviolet radiation by means of sinusoidal modulation of the electrical signal.

Therefore, the objective of this invention is to detect the presence of a living biological element (in a preferred embodiment, the user's finger, which is the biometric recognition element) and distinguish it from one that is not living, using the transmission and reflection properties of pulsed electromagnetic and quasi-coherent radiation on human epithelial tissue (skin and veins).

There are two main characteristics to the invention: the first of these is the integration of a human life detection system with another system, which is a biometric system. This integration is due to its small size and the simplicity of implementing it in hardware. The second basic characteristic is based on the optical spectroscopy principles of transmission and reflection of the pulsed near-infrared and near-ultraviolet radiation on the cutaneous and subcutaneous tissues of the finger (which also imply the absorbance of the infrared radiation by the haemoglobin in the blood and other biological elements). The integration is presented in this document as an added feature of the biometric system for fingerprint detection that functions by radiofrequency. Another crucial characteristic of the invention is also control over the detection of the peaks in the pulsed radiation transmitted and reflected on the finger of the user in question and the detection of the heat emitted (far IR radiation) by the biometric element of the user in question. This detection of the IR and UV radiation is performed by means of an algorithm programmed in C language with a micro-controller.

On the basis of these main characteristics, the biometric sensor is integrated with the life detection system, which detects the radiation transmitted and reflected on the human finger.

It can also function on an autonomous basis as a biometric sensor for personal identification. If the device functions as a complementary life detection element, it lends a much higher level of security to the biometric system in which it is integrated.

The integrated system presents several pairs of quasi-monochromatic light sources that emit on a pulsed basis: two pairs of LEDs with emission bands centred at the near-infrared, a further pair of LEDs with emission bands centred at the UV-A zone of the spectrum and three photodetectors with absorption bands centred at the near-infrared zone of the spectrum and UV-A, which detect the radiation pulses emitted by the LEDs with emission bands centred at the near-IR and UV-A. The biometric element in question (generally the index or middle finger of the user's hand) is positioned between the pulsed emission LEDs and one of the photodetectors with an absorption band at the near-IR, which detects the radiation transmitted through the biometric element.

The electrical signal that feeds the LEDs is controlled in time using the same microcontroller that detects the optical signal. The processing of the optical signal picked up by the photodiodes employs a microcontroller. This microcontroller allows to detect first a level of reference (registration process) for the maximum amplitude of the intensity of each pair of radiation pulses reflected and transmitted on the user's finger and emitted by each pair of sources of quasi-monochromatic radiation sources, so that it is possible to know the variations in amplitude of the optical pulses depending on the emission wavelength of every user that is registered. Moreover, by means of a registration process for many users, it is possible to establish a characteristic human threshold within a confidence interval that is determined by the particular variations of each one. Once the registration process is complete, it is possible to make a comparison with the characteristic human threshold if the device is to be used as a life detection system, whereas the comparison is done 1:1 or 1:N if the device is to be used as a biometric system for personal identification.

The sensor for life detection and/or biometric personal identification may be protected by a semi-cylindrical plastic casing that protects the finger from external light. This plastic casing may also protect the biometric sensor when it is a sensor that is integrated on the inside, such as for example. the radiofrequency sensor for the fingerprint area. Therefore, this protective casing contains the optical elements that constitute the optical device, formed by the light sources and radiation receivers described above. This protective element allows for the finger to be positioned in a characteristic manner and therefore the incident radiation interacts with the living tissue at characteristic points of the biometric recognition element. Its emission-reception system presents optical transmission filters in the near-IR and UV-A ranges, which are also linear polarizers, so that the light detected by the respective photodiodes is lineally polarized.

The control unit for the electrical and optical signals may also be protected by an external casing that is immune to electromagnetic interference and external environments, such as possibly aggressive temperature or humidity conditions. This control unit is electronically connected to the optoelectronic elements that emit and receive the radiation, as well as to the processing unit that contains the registration database used to carry out the comparison process.

The reduced dimensions of the life detection system allows it to be integrated, for example, with a radiofrequency fingerprint sensor (it may also be integrated with any other biometric sensor on the market), so that it allows, in the case of affirmative life detection, to extract the fingerprint map of the user in question, or the map of capillaries on the palm of the user's hand when it is a biometric blood capillary sensor (or the biometric feature that is characteristic of the biometric sensor that is used). Its functioning as a biometric sensor also allows to extract the spectroscopic characteristics, such as the transmittance and reflectance of the user's finger, comfortably and quickly, along with the biometric features if it is integrated with another biometric sensor. Its ergonomic shape means that this biometric sensor is very easy to handle, so that the user does not need any prior learning in order to position their finger in the sensor. Moreover, this is a low-cost system, as the transducing element is optical and hardly increases the product cost. The analysis of the biometric optical information on the user to be identified for comparison with what has already been registered before or in order to ensure that the person being identified by the biometric system in question is alive, is carried out quickly and safely by means of an algorithm that compares signals, located in a processing unit that is connected to the microcontroller.

The main advantage of the integrated biometric sensor described herein is that it allows to detect if the finger belongs to a living person by means of the periodic signal obtained by the pulsed emission of light from the LEDs when it is being transmitted (near-IR emission LEDs) or reflected (near-IR emission LEDs and UV-A emission LEDs) on the finger. Each pair of diodes can emit on an alternate basis, due to a sinusoidal electrical signal introduced in the circuit, which allows for direct, polarized emission by one of the LEDs when the periodic electrical component is positive and allows for the emission of inversely polarized radiation from the other LED when the periodic electrical component is negative. Moreover, the radiation transmittance and reflection values are characteristic of the human tissue biological medium and may therefore be used as biometric parameters for personal identification. This largely eliminates the possibility of the biometric element in question being a replica of the real one (for example, the fingerprint of the user's finger, generally the index finger, which is not from an artificial material such as an inert finger or a silicon hand, or that the blood capillaries pattern is not drawn with infrared paint, etc.), thus ruling out any possible attempt at fraud or usurpation of identity (which is so easy to perpetrate in some biometric sensors, such as the fingerprint sensors offered by the biometric market).

The life detection element inside the biometric unit is an optical device, which means that it is immune to electromagnetic interferences from the external environment, such as might come from the biometric fingerprint sensor (this may use radiofrequency to detect the fingerprint, or electrical capacity or inductance) or from other biometric sensors with which it could be integrated. It may also be located in unfavourable, inhospitable external environments (extreme temperatures, rain or snow, etc.). Sunlight is not a problem for the functioning of this life detection system, despite the fact that it is an optical sensor, because it is protected by the ergonomic casing described above and it uses selective polarizing optical filters.

Therefore, in accordance with an embodiment of the invention, the control unit governs the electrical functions that feed the pairs of light sources. These electrical functions may include periodic alternate electrical signals, so that each pair of light sources emits on an alternate basis.

Moreover, the system in the invention may include resources for receiving the biological element, configured in such a way that when they receive the biological element, said biological element is placed between the pairs of light sources and the photodetectors.

A temperature sensor, which for example is a thermopile, detects the radiating emissivity of the biometric element in question.

On the other hand, the resources for receiving the biological element may include a casing that protects the biological element from external light.

In accordance with another embodiment of the invention, the processing unit contains a database of the pulsed radiation transmitted and reflected in the various biological elements that are registered, which means that the processing unit determines if the biological element is a living biological element by comparing the radiation interpreted by the control unit (which may include a microcontroller) with the elements in the database.

In accordance with a preferred embodiment of the invention, the light sources are as follows:
Pair of LEDs with emission bands centred at $\lambda=1300$ nm and $\lambda=1070$ nm;
Pair of LEDs with emission bands centred at $\lambda=760$ nm and $\lambda=830$ nm;
Pair of LEDs with emission bands centred at $\lambda=385$ nm and $\lambda=375$ nm;
The photodetectors are as follows:
Photodiode with near infrared absorption band centred at $\lambda=780$ nm;
Photodiode with near infrared absorption band centred at $\lambda=1300$ nm;
Photodiode with near-ultraviolet absorption band centred at $\lambda=380$ nm.
and the light-emitting sources and the photodetectors are arranged as follows:
The pairs of LEDs at $\lambda=1300$ nm and $\lambda=1070$ nm, $\lambda=385$ nm and $\lambda=375$ nm and $\lambda=760$ nm and $\lambda=830$ nm are attached to the resource for receiving the biological element and placed facing the photodiode with an absorption band at the near-infrared of the electromagnetic spectrum and centred at λ=780 nm;

A photodiode with an absorption band for near infrared centred at λ=1300 nm is placed between the two LEDs that configure the pair of LEDs with λ=1300 nm and λ=1070 nm;

A photodiode with an absorption band for near UV-A centred at λ=380 nm is placed between the two LEDs that configure the pair of LEDs with λ=375 nm and λ=385 nm.

If the biometric element is a human finger, two sources that emit high-power radiation with the emission band in the near-IR; one centred at λ=880 nm and the other at λ=760 nm, facing two pairs of photodetectors with absorption bands in the near-IR centred at said wavelengths, are positioned on either side of the fingerprint, at a slight slant to the horizontal and facing in the direction of the area of the fingerprint sensor.

The biological element should preferably be a human finger and the LEDs are positioned according to the interaction zone of its emitted light, with the biometric element:

The pair of LEDs with λ1=760 nm and λ2=830 nm are positioned in such a way that the radiation that they emit incides on the first volar ligament of the finger (joint between the first and second phalanges);

The pair of LEDs with λ1=1070 nm and λ2=1300 nm is positioned in such a way that the radiation that they emit incides on the centre of the second phalange of the finger;

The pair of LEDs with λ1=375 nm and λ2=385 nm is positioned in such a way that the radiation that they emit incides on the centre of the first phalange of the finger.

The pair of high power LEDs with λ=880 nm and λ=760 nm is positioned in such a way that the light that is emitted interacts with the fingerprint and the area where the fingerprint sensor is located and is detected by photodetectors with absorption peaks of λ=880 nm and λ=760 nm, which are facing said LEDs.

Moreover, the system may include polarizing filters with transmission bands in infrared and ultraviolet that eliminate the visible component of the electromagnetic spectrum. These polarizing filters may be arranged as follows:

A high-pass linear polarizing filter with a transmission band in the near-IR placed in front of each of the corresponding pairs of LEDs (λ1=780 nm and λ2=830 nm, λ1=1070 nm and λ2=1300 nm) and of the 1300 nm photodiode, whereas this filter linearly polarizes the near-IR component of the electromagnetic spectrum;

A linear polarizing filter with a transmission band in the ultraviolet placed in front of each LED in the corresponding LED pair (λ1=375 nm and λ2=385 nm) and of the 380 nm photodiode, whereas this filter linearly polarizes the near-ultraviolet component of the spectrum;

A linear polarizing filter, with the polarization axis crossing that of the LEDs and with a transmission band in the near-IR, which is placed in front of the photodiode with the near-infrared absorption band centred at λ=780 nm.

Polarizing filters rotated at a 60° angle and positioned in front of the photodiodes that replace the aforementioned polarizing filters and eliminate for the most part the visible and near-IR component from the external environment.

The invention also relates to a biometric sensor for personal identification that contains the system for detecting the presence of a living biological element described above. This biometric sensor could be a fingerprint sensor that operates by radiofrequency.

In accordance with another aspect of the invention, a procedure is provided for detecting the presence of a living biological element, formed by the following stages:

issuing a pulsed electromagnetic radiation with the emission band located in the near-infrared zone of the electromagnetic spectrum;

issuing a pulsed electromagnetic radiation with the emission band located in the near-ultraviolet zone of the electromagnetic spectrum;

detecting the pulsed radiation transmitted and reflected on the biological element, on the basis of the pulsed radiation emitted with the emission band located in the near-infrared zone;

detecting the pulsed radiation transmitted and reflected on the biological element, on the basis of the pulsed radiation emitted with the emission band located in the near-ultraviolet zone;

detecting the temperature of the biometric element on the basis of its emissivity in the infrared, using a temperature sensor;

determining if the biological element is a living biological element, on the basis of the radiation detected.

The stage of determining if the biological element is a living biological element consists of the following substages:

eliminating external environmental factors such as external temperature and external electromagnetic radiation;

obtaining the average threshold that is characteristic of humans;

comparing the radiations detected with the characteristic threshold obtained.

In accordance with another aspect, the invention provides a computer programme that contains programme instructions that run in a computing system for performing the procedure for detecting the presence of a living biological element. This computer programme may be stored on storage media (for example, a ROM memory or the hard disk of a computer) or carried by a carrier wave (for example electrical or optical).

BRIEF DESCRIPTION OF THE DRAWINGS

In order to provide a better understanding of the above, some drawings have been attached, in which on a schematic basis and merely as a non-restrictive example, a practical case of embodiment is represented.

In the drawings.

DESCRIPTION OF A PREFERRED EMBODIMENT OF THE INVENTION

Basically, the invention is based on the transmission properties of quasi-coherent pulsed near-infrared radiation on human epithelial tissue and its absorption by oxidised and deoxidised haemoglobin (25). It is also based on the reflection of near-ultraviolet (24) and pulsed UV-A (23) radiation on human epithelial tissue.

Figure 1:
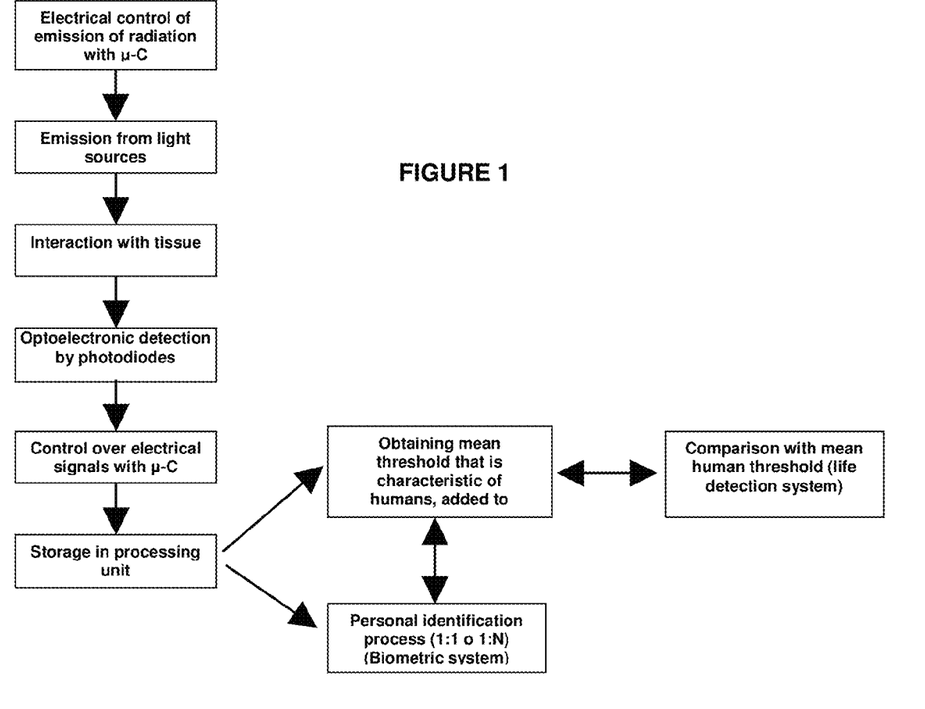
FIG. 1 depicts a flow chart of the procedure for detecting the presence of a living biological element, in accordance with the invention, based on the measurement and identification of the biometric optical information from the interaction of the quasi-coherent pulsed electromagnetic radiation with the biometric element of the user in question (finger on hand)

FIG. 1 presents an outline of the functioning of the invention described above. It is composed of two main parts:

One part that is focused on the field of microelectronics and programming, formed by a microcontroller (which controls the periodic electrical signals that feed the photodiodes and studies the reception of the pulsed optical signs in order to determine if they attain the characteristic human threshold) and a processing unit, connected to said microcontroller, which saves the incoming and analysed biometric data and compares them to biometric data that has already been saved in a biometric database created previously. Thus, in the process of life detection, the comparison is made with the characteristic human average with its confidence interval, while in the case of biometric identification, the comparison may be made with each of the values previously recorded on each user (1:1 or 1:N).

Another part is focused on the field of integrated photonics and formed by light sources with emission bands that are extended in the near-infrared and near-ultraviolet zones of the electromagnetic spectrum and photodetectors with absorption bands that are equivalent to the emission bands in the light sources. These light sources emit pulsed electromagnetic radiation depending on the alternate and periodic electrical signal that feeds them and which is introduced by a microcontroller that has already been programmed. The signals received by the radiation-receiving sources are analysed with TTL logic by the same microcontroller, also programmed, but this time with the task of sending this information, which has already been analysed, to the processing unit, which verifies if the optical signal received is carrying biometric information on an actual biometric element from a living user or if it is a case of fraud using an artificial material.

Figure 2:
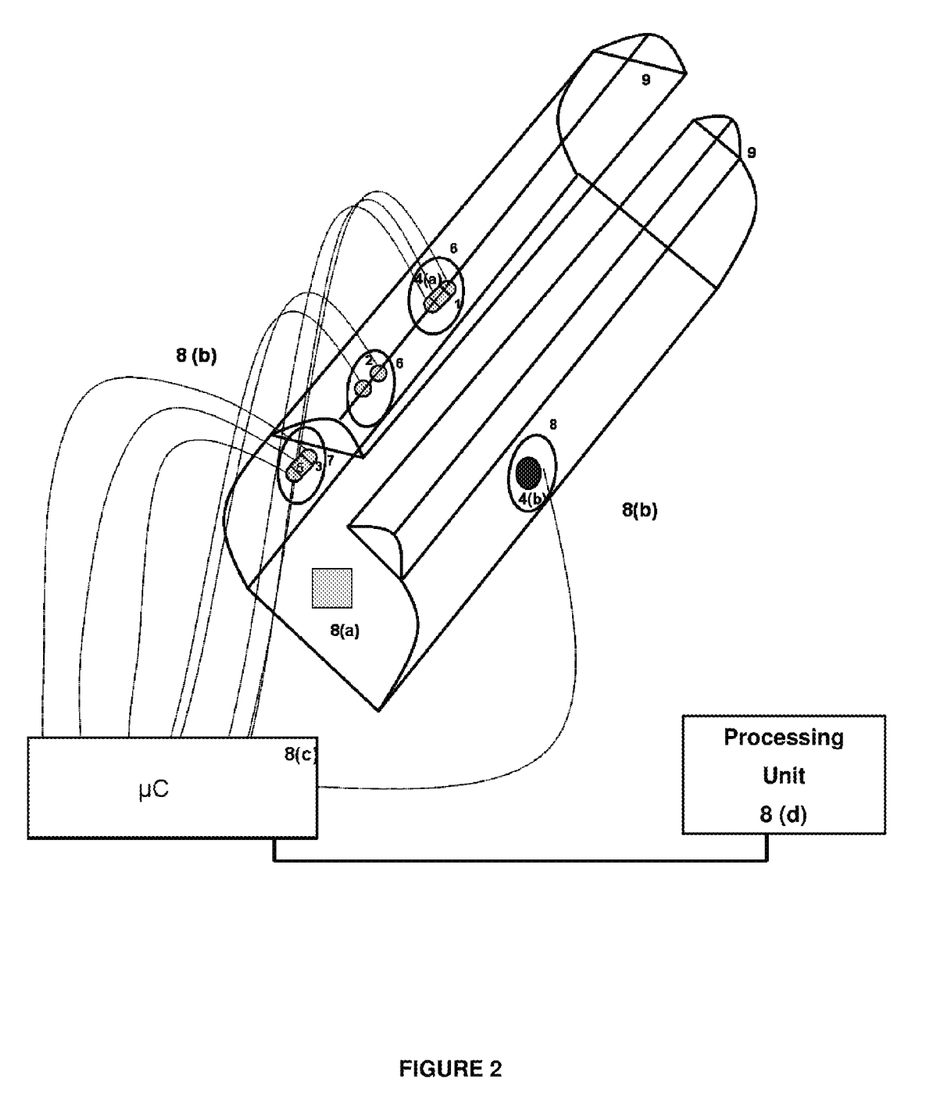
FIG. 2 depicts a schematic representation of the system for detecting the presence of a living biological element, in accordance with the invention.

As may be seen in FIG. 2, the life detection system described herein has three pairs of LEDs with emission bands centred at $\lambda_1=1070$ and $\lambda_2=1300$ (1), $\lambda_3=760$ and $\lambda_4=830$ nm (2) and $\lambda_5=385$ and $\lambda_6=375$ nm (3), two photodetectors with absorption bands centred at the near-infrared zone of the spectrum (4(a) and 4(b)) and UV-A (5), two linear polarizing filters with a transmission band in the near-infrared (6) and a linear polarizing filter with a transmission band in the UV-A zone of the electromagnetic spectrum (7). The linear polarizing filter with the transmission band in the near-IR (6) and positioned beside the pair of LEDs with $\lambda_1=1070$ and $\lambda_2=1300$ (1) polarizes the light captured by its associated photodiode (4(a)). The same thing happens with the UV-A filter (7) and its associated LEDs (3). Another linear polarizing filter (8), with the polarization axis crossed and perpendicular to the polarization axes of the other polarizing filters has a transmission band in the near-IR and is identical to the one associated to the pair of LEDs with $\lambda_3=760$ and $\lambda_4=830$ nm (2). It is positioned beside the photodiode with an absorption band in the near-infrared zone of the electromagnetic spectrum centred at $\lambda=780$ nm (4(b)) and makes it possible to detect the infrared radiation that is transmitted through the finger (and which changes its polarization status) and not another that has not changed it. These optical elements are protected by an ergonomic plastic casing (9) and constitute the optical part of the life detection sensor. Moreover, a thermopile (8(a)) detects the emission of far-IR radiation from the biometric element in question. The other part, which is the electronic component, is formed by a microcontroller (8(c)) that is connected by electrical connections (8(b)) to the optoelectronic elements (light-emitting and receiving sources). As described above, the microcontroller governs the electrical functions (which are periodic alternate) that feed the optical emitting sources and interprets the pulsed signals that are transmitted or reflected on the user's finger, which have been captured by the receiving sources, which are the photodiodes. The processing unit (8(d)) saves all of the optical signals that have been transmitted and reflected by the fingers of the various registered users and they are compared to the new incomers, which are previously analysed by the microcontroller. Thus these incoming optical signals may be used as a life detection system as long as the microcontroller detects them as being valid and sends them to the processing unit that is in charge of deciding if they attain the characteristic human threshold or if, on the contrary, they correspond to a fraud attempt.

Figure 3:
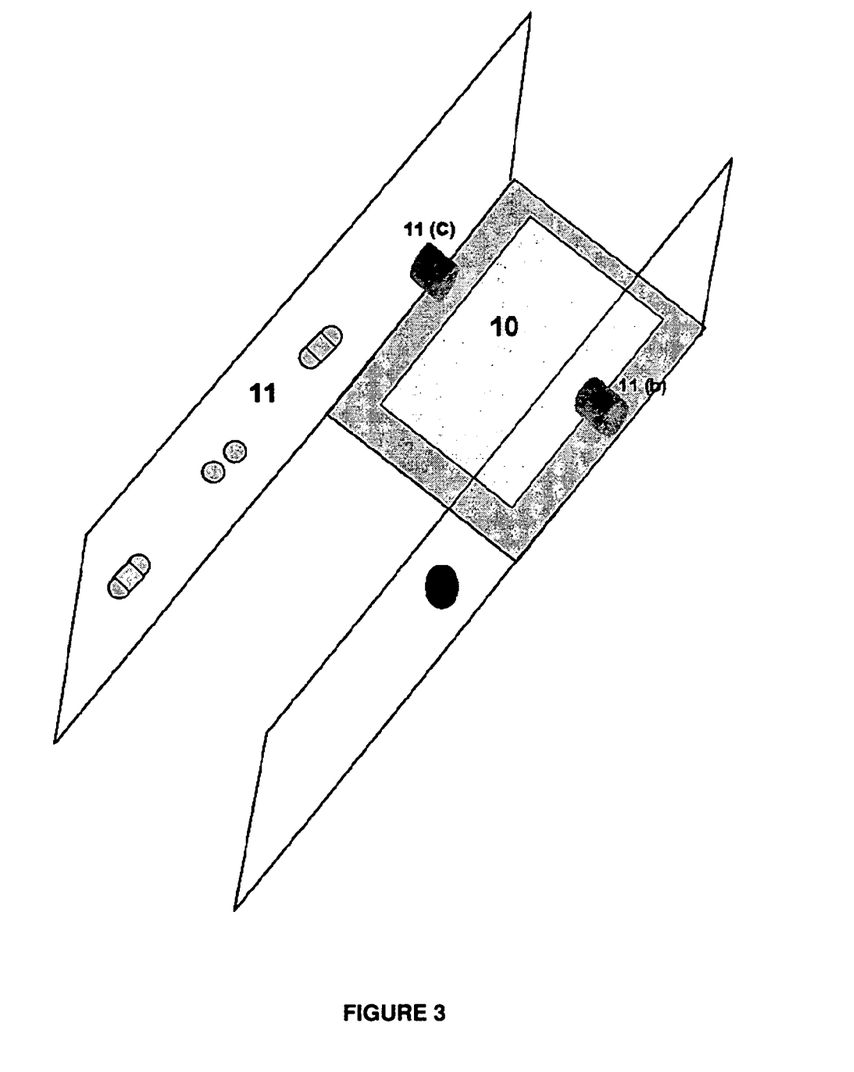
FIG. 3 depicts a schematic representation of the system to detect the presence of a living biological element in FIG. 2, to which a biometric finger sensor is incorporated.
Figure 4:
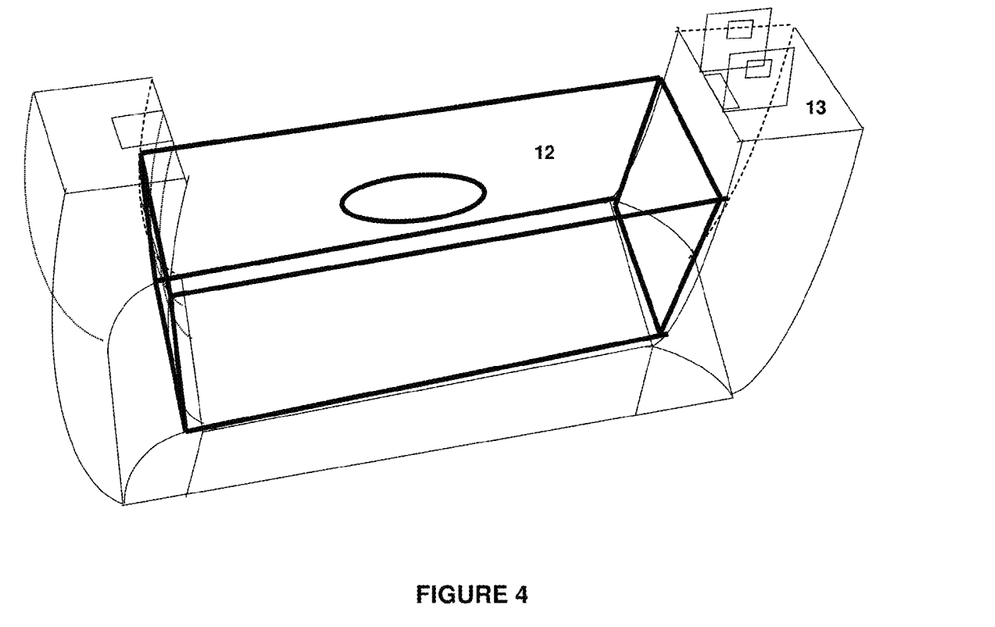
FIG. 4 depicts a schematic representation of the biometric sensor for detecting life in FIG. 2, included in a biometric sensor for reading the capillary map on the palm of the hand.

In these cases, the system is usually integrated in a biometric sensor for personal identification, such as the fingerprint or blood capillary systems, as demonstrated in FIGS. 3 and 4 and which starts to function when the life detection element confirms that the user with their characteristic biometric element is alive. Moreover, if it is integrated with a fingerprint sensor, near-IR radiation emitting sources are incorporated facing photodiodes with the same band, but for absorption, (11(b) and 11(c)), which allow to distinguish a false fingerprint from an authentic one. On the contrary, it may be desirable for the detection sensor to function as an independent biometric sensor for independent personal identification, without being related to any other biometric system, so that the electromagnetic radiation signals transmitted and reflected on the finger in question are considered to be unique features that are unrepeatable and therefore, the system becomes a biometric sensor where the processing unit performs the processes of registration, identification and verification of the user placing their finger on this aforementioned sensor.

Figure 5:
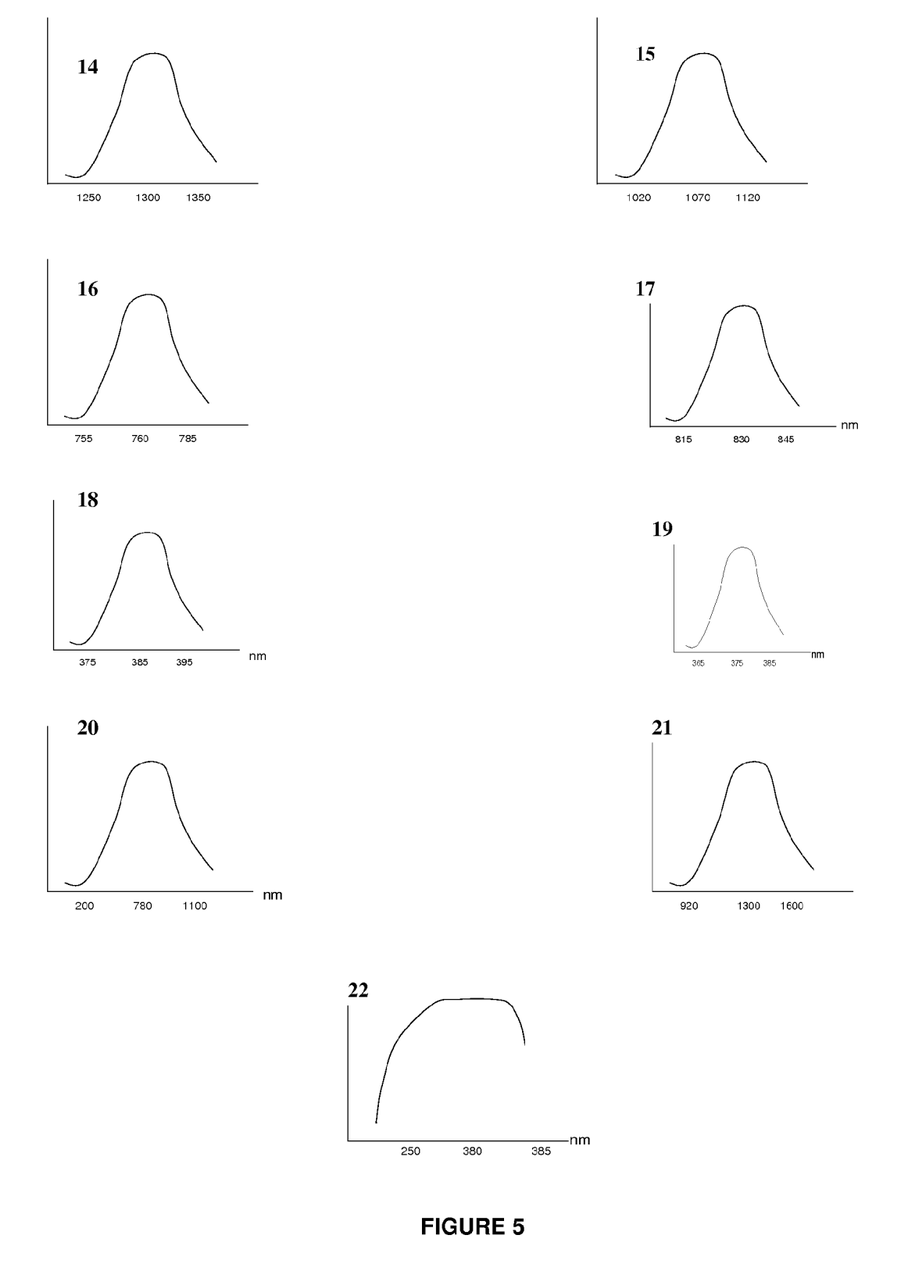
FIG. 5 depicts a graphic representation of the emission spectrums of the LEDs and the receiver photodiodes used.

FIG. 5 depicts the emission spectrums of each of the light sources (14-19), as well as the absorption spectrums of the photodetectors (20-22). These spectrums largely condition the transmission and reflection spectrums obtained from the UV-A radiation (23) and the near-infrared radiation (24,25) with the human finger (FIG. 6) and which are used to choose the light-emitting sources that are most convenient for the biometric application described herein.

Figure 6:
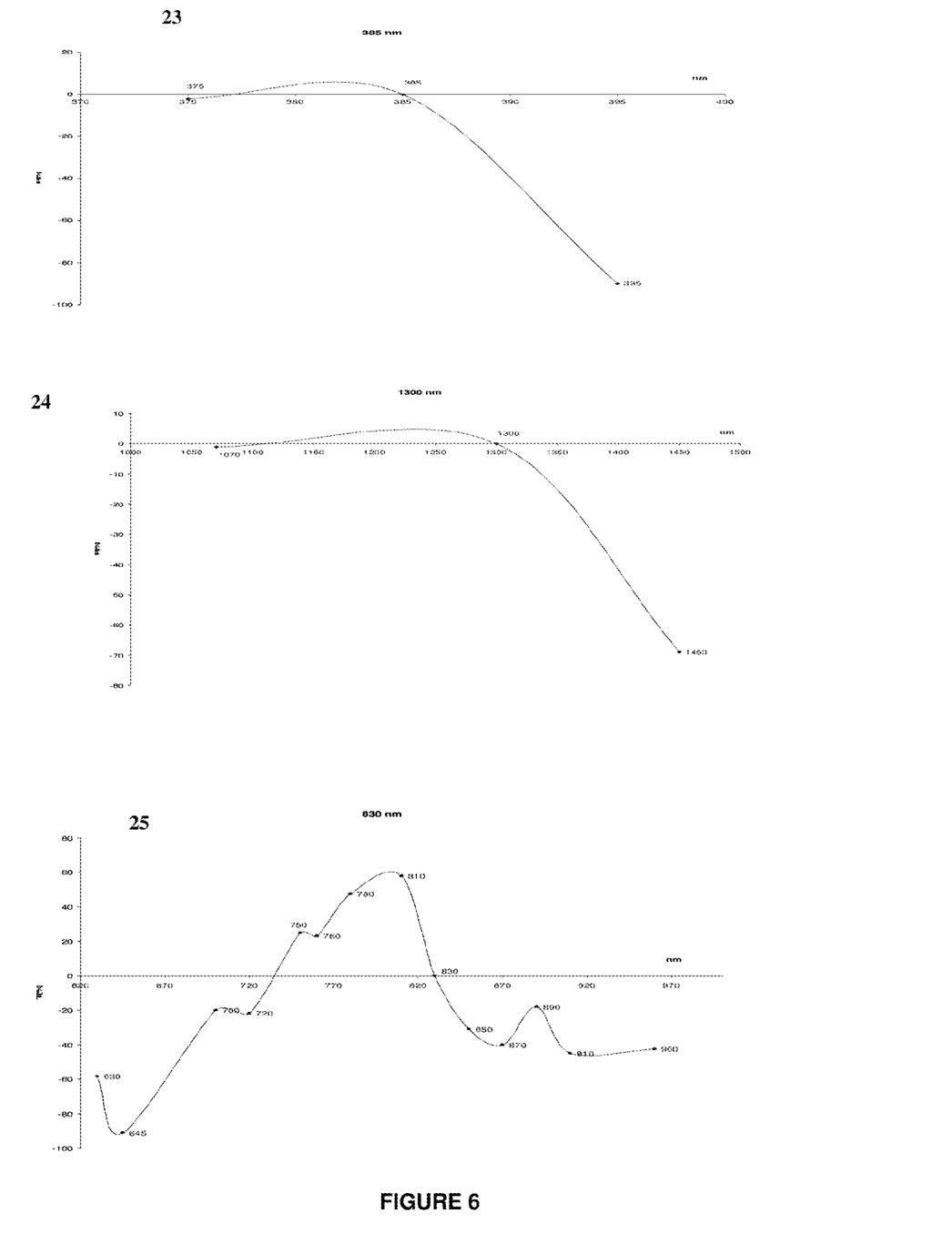
FIG. 6 presents a graphic representation of the spectrums for reflection of near-IR and UV-A radiation and for transmittance of near-IR radiation on the human finger.

Therefore, on the basis of the UV-A transmission and reflection spectrums of the UV-A radiation (23) and of the near-infrared radiation (24, 25) on the human finger, which may be observed in FIG. 6, light sources are chosen to ensure that they are the most suitable for obtaining pairs of light sources with different wavelengths that present very similar values for transmission and reflection on the epithelial tissue of the human finger (1-3). Their values have to be very similar for each pair of LEDs, but not identical, so that the algorithm for detecting the intensity of the radiation is simplified.

The emission wavelengths of the pairs of light sources are as follows:

the pair of LEDs with λ1=760 y λ2=830 nm (2) are in position for the subsequent detection of the intensity of the infrared radiation transmitted by the finger;

the pair of LEDs with λ3=1070 and λ4=1300 (1) are in positioned for the subsequent detection of the intensity of the infrared radiation reflected by the finger;

the pair of LEDs with λ3=375 nm and λ4=385 nm (3) are in position for the subsequent detection of the intensity of the UV-A radiation reflected by the finger.

The positions of each pair of LEDs as regards the biometric element in question, i.e. the index or middle finger, are as follows, depicted in FIG. 7:

the pair of LEDs with λ1=760 nm and λ2=830 nm (2) is positioned so that the radiation that it emits incides on the first volar ligament (joint between the first and second phalange);

the pair of LEDs with λ1=1070 nm and λ2=1300 nm (1) is positioned so that the radiation that it emits incides on the centre of the second phalange;

the pair of LEDs with λ1=375 nm and λ2=385 nm (3) is positioned so that the radiation that it emits incides on the centre of the first phalange.

As demonstrated in FIG. 2, the three pairs of LEDs are placed facing the photodiode that has its absorption band centred at 780 nm (4) and which detects the intensity of the near-infrared radiation transmitted through the volar ligament, which is emitted by the LEDs with emission bands centred at λ1=760 nm and λ2=830 nm (2). Between each remaining pair of LEDs ((3) and (1)) are placed the UV photodiode (with the absorption band centred at λ=380 nm) that detects the UV-A radiation reflected in the area of the finger corresponding to the first phalange (5) and the near-infrared radiation photodiode (4(*a*)) (with absorption band centred at λ=1300 nm and selective, with bandwidth between 920 nm and 1600 nm) that detects the near-IR radiation reflected on the second phalange of the finger and emitted by the pair of LEDs with λ1=1070 nm and λ2=1300 nm (1), respectively.

Figure 7:
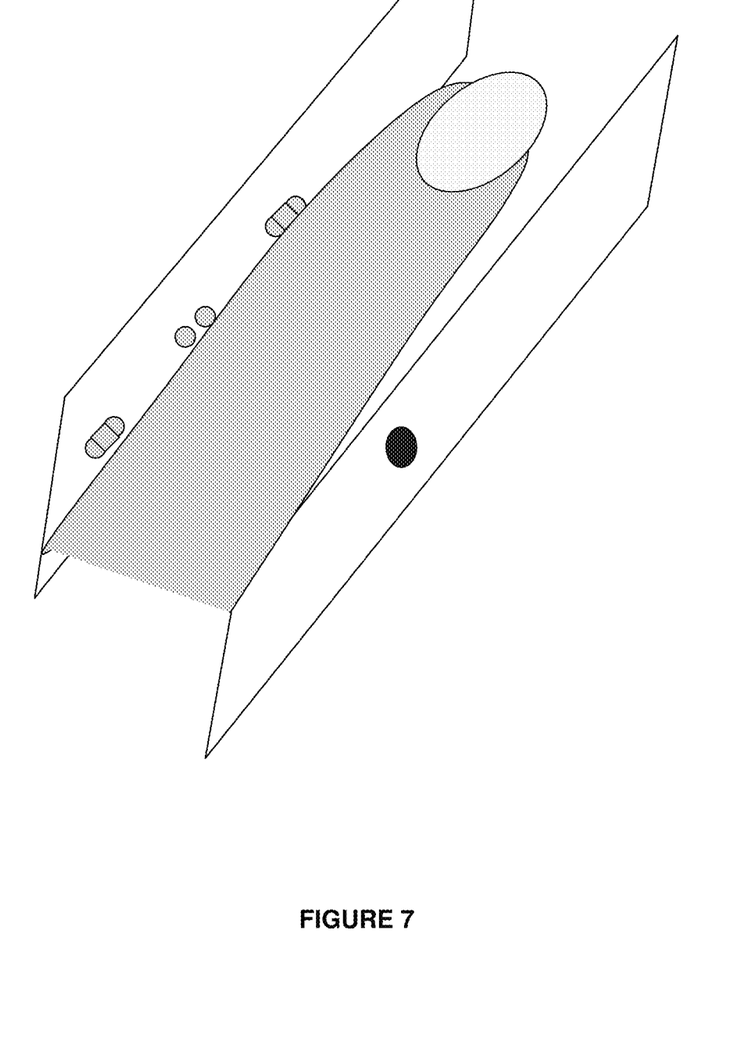
FIG. 7 depicts a schematic representation of how the system in FIG. 2 receives a user's finger for identification.

Therefore, FIG. 7 depicts the case of a fingerprint sensor (10), in which the biometric element in question is the fingerprint of a finger on the human hand that is positioned over its sensory area, located inside an ergonomic protective casing (9). Thus, this biometric sensor registers the user by obtaining their fingerprint pattern. Prior to obtaining this biometric pattern, the life detection system starts to function on a sequential basis by means of the emission of the radiation from each pair of LEDs (1-3) with the wavelengths described above. This radiation is transmitted and reflected on the epithelial tissue of the finger of the user in question and absorbed by the haemoglobin (23-25). Once life has been detected, the transmittance and reflectance signals may be used, along with the fingerprint pattern, as complementary biometric data on the user being registered.

The mathematical model for the life detection system is based on measuring the time in which the light intensity passes through fine tissue, such as through the fingertip for example, and it depends on the wavelength of the incident radiation. The signal process is based on this simple model and on Beer-Lambert's Law:

$$I(\lambda,t)=I_0(\lambda)\cdot e^{-\alpha\cdot z} \quad (1)$$

where α is the molar absorption or absorbance coefficient for the epithelial tissue in the human finger, which depends on the wavelength λ of the incident radiation, by means of the following expression:

$$\alpha = \frac{4\pi k}{\lambda} \quad (2)$$

where α is the extinction coefficient of the epithelial tissue in the human finger.

Therefore, equation (1) shows that the distance that the electromagnetic radiation penetrates in the human body depends on the wavelength of the incident radiation and the medium in which the light penetrates. This is the reason why the values for transmission and reflection of the near-infrared and UV-A radiation on the human finger are used as a biometric system for identification, as each person has their individual capillary pattern and characteristic tissue medium, as well as their typical thickness.

The mathematical expression used in the functioning of a conventional pulsioximeter is as depicted in the equation (3)

$$I(\lambda, t) = I_o(\lambda) \cdot e^{-(\sum_v (\sigma_{Hb_v}(\lambda) s_{Hb_v})) z(t)} \quad (3)$$

where $I_0$ is the intensity and λ is the wavelength of the incident light, c(λ) is the concentration and $s_{Hb}(\lambda)$ is the absorption coefficient of the wavelength depending on each haemoglobin derivative (Hb) and z describes the variable thickness.

Therefore, this life detection system may also be used as a pulsioximeter, simply by incorporating another pair of LEDs with wavelengths $\lambda_1$=630 nm and $\lambda_2$=940 nm. The concentration of the oxygen saturation in the blood is defined as the quotient between the total level of oxidised haemoglobin in the blood and the total haemoglobin level (oxygenated and reduced). It is expressed by the following equation:

$$SaO_2 = \frac{HbO_2}{\text{Total Haemoglobin}} \quad (4)$$

Human body tissues absorb different intensities of radiation depending on the degree of oxidation of the blood that passes through them, as expressed by Lambert's Law. As described above, the pulsioximeter uses radiation within the near-infrared band of the electromagnetic spectrum, in our case, with bandwidths of $\lambda_1$=630 nm and $\lambda_2$=940 nm. If we use the signals from both bandwidths, the concentration of saturated oxygen in the blood may be mathematically simplified as follows:

$$R' \propto SaO_2 = \frac{\log(I_{ac})\lambda_1}{\log(I_{ac})\lambda_2} \quad (5)$$

Where bandwidths $\lambda_1$ and $\lambda_2$ are $\lambda_1$=630 nm and $\lambda_2$=940 nm and $I_{ac}$ is the intensity absorbed by the tissue and blood capillaries.

Figure 8:
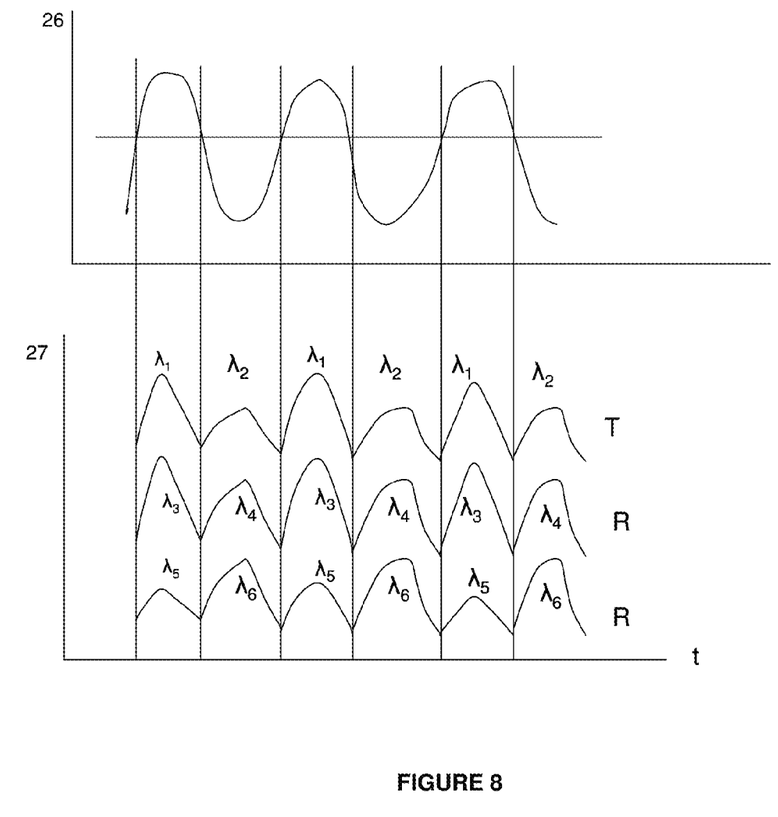
FIG. 8 depicts a graphic representation of the periodic electrical signals that feed each pair of LEDs, as well as the optoelectronic signals detected by the photodiode.

FIG. 8 depicts the electrical signal (26) that feeds the LEDs and the optical signal (27) that is captured by the photodiodes. This electrical signal is sequential, sinusoidal and symmetrical (26). Half its amplitude is in a positive voltage value (V>0), whereas its other half is in a negative value (V<0), meaning that the LEDs in each pair of LEDs light up on an alternate, periodic basis (27). This means that the photodiodes detect the pulses transmitted and reflected on the finger, for each wavelength of each of the pairs in question. Because the electrical supply is sequential, sinusoidal and symmetrical, the detection of light by the photodiodes is also sequential, sinusoidal and symmetrical (27), so that each complete period of the light signal detected by the characteristic photodiode corresponds to the radiation emitted by one of the LEDs that are illuminated in the corresponding pair of LEDs, while the second period of the signal detected corresponds to the other one. These signals also present different amplitudes, although the greatest possible similarity has been sought. Each pair of LEDs has one directly polarized LED and the other inversely polarized, meaning that the signal detected by the photodiode (27) is periodic with a period that is double that of the electrical supply signal, meaning that one is on while the other is off and vice-versa.

Figure 9:
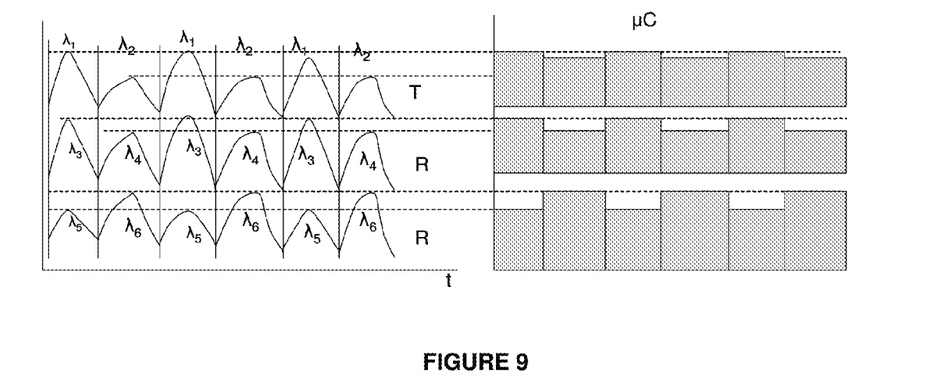
FIG. 9 depicts a graphic representation of the optoelectronic signal detected by the photodiode for a particular user that is taken as the reference level for the controller.

FIG. 9 depicts how the microcontroller detects the signal received by the photodiodes (optical signal transmitted and reflected on the finger of a user in question) for each pair of LEDs in the system. If this signal is considered to be the average reference signal (average of signals registered) and as long as its maximum amplitude is reached, it is considered to be a characteristic human value for the transmission and reflection of the radiation on the finger of the user in question, by means of a mathematical algorithm and using TTL logic.

Several measurements of the transmittance and reflectance of near-infrared and near-ultraviolet radiation have been made for the middle finger of several users and it has been observed that there is a light margin of error (confidence interval) in the average maximum amplitude of the signal detected by the photodiodes (28) and (29), which is considered by the microcontroller to be valid in order to proceed to identify the user.

Figure 10:
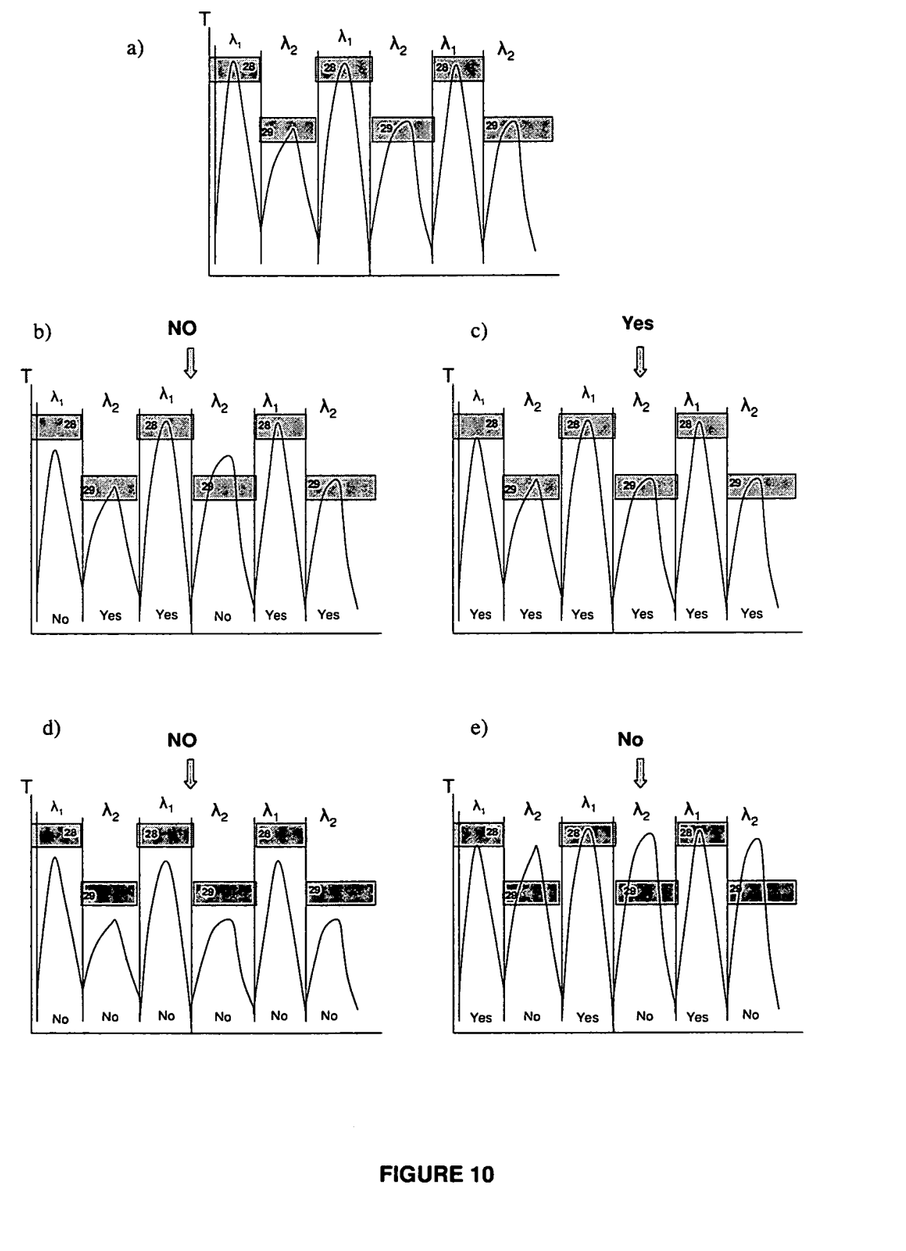
FIG. 10 depicts a graphic representation of how the controller accepts or refuses the identification of the user in question.

This is depicted in FIG. 10, which shows the pattern of amplitudes of reference for the microcontroller with their margin of error (a). Therefore, if some of the pulses in the sequence of the pulse train emitted by the LEDs in each pair of LEDs and detected by the photodiodes do not attain the threshold of reference with their confidence interval to be detected ((b), (d) and (e)), the microcontroller by TTL logic takes these pulses to be 0 and they are not detected. This information is sent to the processing unit, which programmes a message addressed to the user interface, which tells the user to position their finger correctly in the sensor, as it considers that there is an attempted fraud (if the device is operating as a life detection element) or that the identification has failed because the optical signal that has been received and transduced does not exist in the database (if the device is operating as an autonomous biometric sensor for personal identification, without the need for it to be coupled to another biometric sensor). However, if the incoming biometric signal coincides with the pulse train of reference (within the confidence interval that is characteristic of the biometric device) (c), access will be permitted or there will be a signal of life detected.

As mentioned previously, the biometric information that is detected may be used for biometric identification of the user or simply as a means for detecting life, so that its associated integrated biometric sensor ((10) and (12)) functions whenever the life detection signal is within the human optical range.

Therefore, FIG. 10 represents the following:

1. Confidence interval allowed (obtained by registering several users) so that within same the microcontroller will consider the reflection or transmission signal detected by the photodiode and emitted by one of the LEDs in each pair of LEDs in the described device to be valid.
2. Confidence interval allowed so that within same the microcontroller will consider the reflection or transmission signal detected by the photodiode and emitted by the other LED in each pair of LEDs in the described device to be valid.
    a) Average optoelectronic signal for all users registered and detected by the photodiode, with its confidence interval, which is taken as a level of reference for the controller
    b) If some of the light pulses do not attain the confidence interval registered as valid reference identification (erroneous identification or negative life signal)
    c) If some of the light pulses attain the confidence interval registered as valid reference identification (valid identification or positive life signal)
    d) If some of the light pulses do not attain the confidence interval registered as valid reference identification (erroneous identification or negative life signal)
    e) If some of the light pulses do not attain the confidence interval registered as valid reference identification (erroneous identification or negative life signal Despite the fact that this text has described and represented a preferred embodiment of this invention, it is evident that an expert in the matter may introduce variations and changes or replace the details by others that are technically equivalent, without leaving the sphere of protection defined by the claims attached hereto.

Moreover, despite the fact that the embodiments described for the invention, with reference to the Figure, include computing systems and processes carried out in computing systems, the invention is also extended to computer programmes, more specifically computer programmes in or on carrier media that have been adapted for the purpose of implementing the invention. The computer programme may be in the form of source code, object code or in a code that is half-way between source code and object code, such as in partially compiled form or any other that is suitable for using in the implementation of the processes in accordance with the invention. The carrier medium may be any entity or device that is capable of carrying the programme.

For example, the carrier medium may constitute a storage medium, such as a ROM, for example a CD ROM or a semiconductor ROM, or a magnetic recording medium, for example a floppy disk or a hard disk. The carrier medium may also be a transmissible carrier medium, such as an electrical or optical signal that may be transmitted via electrical or optical cable, radio or other means.

When the computer programme is contained in a signal that may be transmitted on a direct basis through a cable or other device or medium, the carrier medium may be constituted by this cable or other device or medium.

Alternatively, the carrier medium may be an integrated circuit in which the computer programme is embedded, whereas said circuit is integrated for performing the relevant processes or may be used to perform same.

The invention claimed is:
1. An optical system for detecting a presence of a living biological element, comprised of
    at least one pair of light sources (1; 2; 3) that emit pulsed electromagnetic radiation with an emission band located in a near-infrared zone of the electromagnetic spectrum;

at least one pair of light sources (1; 2; 3) that emit pulsed electromagnetic radiation with an emission band located in a near-ultraviolet zone of the electromagnetic spectrum;

at least one photodetector (4) with an absorption band located in the near-infrared zone of the electromagnetic spectrum, for detecting the pulsed radiation transmitted and reflected on the biological element, on a basis of the pulsed radiation emitted by the pair of light sources that emit the radiation with the emission band located in the near-infrared zone;

at least one photodetector (5) with an absorption band located in the near-ultraviolet zone of the electromagnetic spectrum, for detecting the pulsed radiation reflected on the biological element, on a basis of the pulsed radiation emitted by the pair of light sources (1; 2; 3) that emit the radiation with the emission band located in the near-ultraviolet zone;

a control unit (8(*c*)), connected to the pairs of light sources and to the photodetectors, which interprets the pulsed radiation transmitted and reflected on the biological element and detected by the photodetectors; and a processing unit (8(*d*)), connected to the control unit, which determines if the biological element is a living biological element, on a basis of the radiation interpreted by the control unit, and by an emission of a periodic signal obtained by the pulsed radiation emission of the pairs of light sources on an alternate basis, due to a sinusoidal electrical signal configured for the emission of the pairs of light sources.

2. System according to claim 1, wherein the control unit (8(*c*)) governs a plurality of electrical functions that feed the pairs of light sources (1; 2; 3).

3. System according to claim 2, wherein the electrical functions are comprised of periodic alternate electrical signals, so that each pair of light sources (1; 2; 3) emits on an alternate basis.

4. System according to claim 1, wherein the biological element is one of a user's fingers.

5. System according to according to claim 1, further including a means for receiving the biological element, configured in such a way that when it receives the biological element, said biological element is arranged between the pairs of light sources and the photodetectors.

6. System according to claim 5, wherein the means for receiving the biological element are comprised of a casing (9) that protects the biological element from external light.

7. System according to claim 1, wherein the processing unit (8(*d*)) contains a database of the pulsed radiation transmitted and reflected on various biological elements that have been registered and the processing unit determines if the biological element is a living biological element by comparing the radiation interpreted by the control unit (8(*c*)) to the elements in the database.

8. System according to claim 1, wherein the control unit (8(*c*)) includes a microcontroller.

9. System according to claim 1, wherein the light sources comprise:
a pair of LEDs with emission bands centred at $\lambda=1300$ nm and $\lambda=1070$ nm;
a pair of LEDs with emission bands centred at $\lambda=760$ nm and $\lambda=830$ nm;
a pair of LEDs with emission bands centred at $\lambda=385$ nm and $\lambda=375$ nm.

10. System according to claim 1, wherein the photodetectors comprise:

a photodiode with near infrared absorption band centred at $\lambda=780$ nm;
a photodiode with near infrared absorption band centred at $\lambda=1300$ nm;
a photodiode with near-ultraviolet absorption band centred at $\lambda=380$ nm.

11. System according to claim 9, wherein the light-emitting sources and the photodetectors are arranged as follows:
the pairs of LEDs with $\lambda=1300$ nm and $\lambda=1070$ nm, $\lambda=385$ nm and $\lambda=375$ nm and $\lambda=760$ nm and $\lambda=830$ nm are attached to the means for receiving the biological element and facing a photodiode with the absorption band in the near-infrared zone of the electromagnetic spectrum and centred at $\lambda=780$ nm;
a photodiode with its near-infrared absorption band centred at $\lambda=1300$ nm is positioned between the two LEDs that configure the pair of LEDs with $\lambda=1300$ nm and $\lambda=1070$ nm;
a photodiode with its near UV-A absorption band centred at $\lambda=380$ nm is positioned between the two LEDs that configure the pair of LEDs with $\lambda=375$ nm and $\lambda=385$ nm;
for an associated biometric sensor that is a biometric fingerprint sensor, two sources emitting high-power radiation with the emission band in the near-IR, one centred at $\lambda=880$ nm and the other at $\lambda=760$ nm, facing two pairs of photodetectors with absorption bands in the near-IR centred at said wavelengths, are positioned on either side of the fingerprint, at a slight angle to a horizontal and facing in a direction of a sensory area of the fingerprint sensor.

12. System according to claim 9, wherein the biological element is a human finger and the LEDs are positioned according to an interaction zone of the light that they emit, with the biometric element:
the pair of LEDs with $\lambda1=760$ nm and $\lambda2=830$ nm are positioned so that the radiation that they emit is incident on a first volar ligament of the finger (joint between a first and second phalanges);
the pair of LEDs with $\lambda1=1070$ nm and $\lambda2=1300$ nm are positioned so that the radiation that they emit is incident on the centre of the second phalange of the finger;
the pair of LEDs with $\lambda1=375$ nm and $\lambda2=385$ nm are positioned so that the radiation that they emit is incident on the centre of the first phalange of the finger;
the pair of high-power LEDs with $\lambda=880$ nm and $\lambda=760$ nm are positioned so that the light that is emitted interacts with the fingerprint and the sensory area of the fingerprint sensor and is detected by photodetectors with absorption peaks of $\lambda=880$ nm and $\lambda=760$, which are placed opposite said LEDs.

13. System according to claim 9, further comprising a plurality of polarizing filters (6, 7, 8) with transmission bands in an infrared and ultraviolet, which eliminate a visible component of the electromagnetic spectrum.

14. System according to claim 13, wherein the polarizing filters are arranged as follows:
a high-pass linear polarizing filter with a transmission band in the near-IR placed opposite each one of the corresponding pairs of LEDs ($\lambda1=780$ nm and $\lambda2=830$ nm, $\lambda1=1070$ nm and $\lambda2=1300$ nm) and a 1300 nm photodiode, whereas said filters linearly polarizes the IR component of the electromagnetic spectrum;
a linear polarizing filter with a transmission band in the ultraviolet placed opposite each LED in the corresponding pairs of LEDs ($\lambda1=375$ nm and $\lambda2=385$ nm) and a 380 nm photodiode, whereas said filter linearly polarizes the near-ultraviolet component of the spectrum;

a linear polarizing filter, with the polarization axis crossing that of the LEDs and with a transmission band in the near-IR, which is placed in front of a photodiode with the near-infrared absorption band centred at λ=780 nm;

the polarizing filters rotated at a 60° angle and positioned in front of the photodiodes that replace the aforementioned polarizing filters and eliminate for the most part the visible and near-IR component from the external environment.

15. System according to claim 1, further comprising a thermopile for detecting the emissivity of far-IR radiation in a biometric element in question.

16. Biometric sensor for personal identification, comprising of a system for detecting the presence of a living biological element according to claim 1.

17. Biometric sensor according to claim 16, configured as a fingerprint sensor that operates by radiofrequency.

18. Procedure for detecting a presence of a living biological element, comprising the steps of:

issuing a pulsed electromagnetic radiation with an emission band located in a near-infrared zone of the electromagnetic spectrum;

issuing a pulsed electromagnetic radiation with an emission band located in a near-ultraviolet zone of the electromagnetic spectrum;

detecting pulsed radiation transmitted and reflected on the biological element, on a basis of the pulsed radiation emitted with the emission band located in the near-infrared zone;

detecting pulsed radiation reflected on the biological element, on a basis of the pulsed radiation emitted with the emission band located in the near-ultraviolet zone;

detecting a temperature of a biometric element on a basis of its emissivity in an infrared, by means of a temperature sensor;

emitting a periodic signal obtained by the pulsed near-infrared and near ultra-violet radiation emissions on an alternate basis, due to a sinusoidal electrical signal configured for both the radiation emissions;

determining if the biological element is a living biological element, on a basis of the radiation detected.

19. Procedure according to claim 18, wherein the step of determining if the biological element is a living biological element comprises the substeps of:

eliminating external environmental factors such as external temperature and external electromagnetic radiation;

obtaining an average threshold that is characteristic of humans;

comparing the radiations detected with a characteristic threshold obtained.

20. A non-transitory computer-readable medium having stored thereon a computer program that includes programming instructions that run in a computing system for performing the procedure according to claim 18.

21. A non-transitory computer-readable medium having stored thereon a computer program that includes programming instructions that run in a computing system for performing the procedure according to claim 19.

* * * * *